United States Patent [19]

Berman et al.

[11] Patent Number: 4,863,785

[45] Date of Patent: Sep. 5, 1989

[54] NONWOVEN CONTINUOUSLY-BONDED TRILAMINATE

[75] Inventors: Mark H. S. Berman; Dilip D. Doshi, both of Simpsonville; Thomas F. Gilmore, Greer, all of S.C.

[73] Assignee: The James River Corporation, Richmond, Va.

[21] Appl. No.: 273,034

[22] Filed: Nov. 18, 1988

[51] Int. Cl.$^4$ .............................................. B32B 7/02
[52] U.S. Cl. ..................................... 428/218; 428/212; 428/213; 428/284; 428/287; 428/296; 428/297; 428/298; 428/903
[58] Field of Search ............... 428/903, 296, 297, 298, 428/172, 284, 287, 212, 213, 218

[56] References Cited

U.S. PATENT DOCUMENTS

| | | | |
|---|---|---|---|
| 3,542,634 | 11/1970 | Such et al. | 428/296 |
| 3,788,936 | 1/1974 | Brock et al. | 428/296 |
| 4,039,711 | 8/1977 | Neuman | 428/296 |
| 4,041,203 | 8/1977 | Brock et al. | 428/296 |
| 4,196,245 | 4/1980 | Kitson et al. | 428/198 |
| 4,374,888 | 2/1983 | Bornslaeger | 428/296 |
| 4,436,780 | 3/1984 | Hotchkiss et al. | 428/296 |
| 4,493,868 | 1/1985 | Meitner | 428/296 |
| 4,508,113 | 4/1985 | Maloney | 428/212 |
| 4,555,811 | 12/1985 | Shimalla | 428/212 |
| 4,766,029 | 8/1988 | Brock et al. | 428/296 |

Primary Examiner—James J. Bell
Attorney, Agent, or Firm—Finnegan, Henderson, Farabow, Garrett & Dunner

[57] ABSTRACT

A nonwoven composite material comprising a meltblown fabric layer of a thermoplastic polymer sandwiched between two prebonded, spunbonded reinforcing fabric layers of a thermoplastic polymer, all continuously-bonded together to form a composite material. The preferred thermoplastic polymer for both the meltblown and spunbonded layers is polypropylene. The nonwoven composite material contains a minimal number of loose fibers, is highly resistant to the penetration of liquids and would also be expected to exhibit good abrasion resistance, while maintaining tear resistance and softness comparable to non-prebonded materials characterized by discrete bonding patterns. The nonwoven composite material is especially useful as a sterilization wrap for surgical and other health care items.

10 Claims, 2 Drawing Sheets

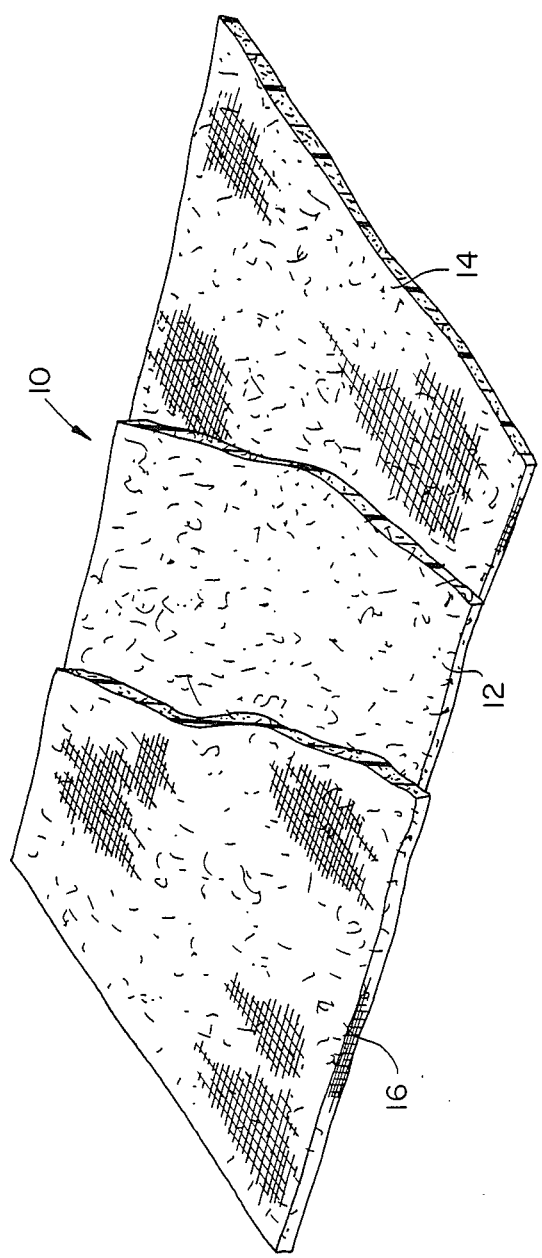

NONWOVEN CONTINUOUSLY-BONDED TRILAMINATE

BACKGROUND OF THE INVENTION

1. Field of the Invention

The present invention relates to nonwoven fabrics and, more particularly, to a nonwoven composite material which comprises a meltblown fabric layer of thermoplastic polymeric microfibers sandwiched between two prebonded reinforcing fabric layers of thermoplastic polymeric filaments, the three layers being continuously-bonded together to form a fabric material.

2. Description of the Prior Art

A wide range of nonwoven fabric laminates that incorporate meltblown materials are known. Such fabrics have been produced using a variety of lamination procedures.

U.S. Pat. No. 4,374,888 to Bornslaeger discloses a class of such laminates that are useful as recreational fabrics. U.S. Pat. No. 4,436,780 to Hotchkiss et al. discloses a meltblown-containing laminate for use as a wiper. U.S. Pat. No. 4,196,245 to Kitson et al. discloses a composite material having at least two meltblown fabric layers that is said to be useful as surgical gowns, surgical drapes, and the like. The Bornslaeger, Hotchkiss et al., and Kitson et al. fabrics are produced by point-bonding processes.

U.S. Pat. No. 4,041,203 to Brock et al. discloses a nonwoven fabric-like material that comprises a meltblown fabric and a web of substantially continuous and randomly deposited molecularly oriented filaments of a thermoplastic polymer. The web is not prebonded and thus has no integrity of its own until it is bonded to the meltblown fabric. The fabric and the web are point-bonded together to obtain a material that is said to have desirable strength characteristics and to possess a textile-like appearance, drape, and hand.

U.S. Pat. No. 3,795,571 to Prentice discloses a nonwoven fabric laminate comprising a meltblown microfiber mat that has high strip tensile strength, bonded to at least one other mat that has high tear resistance. The laminate can be formed by point-bonding or by adhesive bonding.

U.S. Pat. No. 4,508,113 to Malaney discloses five-ply disposable drapes that incorporate meltblown material. U.S. Pat. No. 4,555,811 to Shimalla discloses a nonwoven meltblown-containing laminate structure useful as an operating room gown. The Malaney and Shimalla laminates are made on a heated embossing calendar.

SUMMARY OF THE INVENTION

It is an object of the present invention to provide a nonwoven composite material which contains a minimal amount of loose fibers.

It is another object of the present invention to provide a nonwoven composite material that has good abrasion resistance.

It is another object of the present invention to provide a continuously-bonded nonwoven composite material that has comparable tear resistance to discretely bonded nonwoven composites.

It is another object of the present invention to provide a continuously-bonded nonwoven composite material that has comparable softness or stiffness to point-bonded nonwoven composites.

It is another object of the present invention to provide a nonwoven composite material in which the fiber materials, nonwoven web types and basis weights of the reinforcing web layers can be manipulated to enable the formation of a nonwoven composite material that possesses the particular properties desired.

A further object of the present invention is to provide a nonwoven composite material which is capable of being used as a sterilization wrap in the medical field.

It is a further object of the invention to provide a material for use as a sterilization wrap that will permit penetration of a sterilant such as steam while impeding the passage of bacteria and other contaminants.

It is a further object of the invention to provide a material for use as a sterilization wrap that is hydrophobic and also minimizes the penetration of liquids through the wrap.

The present invention, as embodied and broadly described herein, overcomes the problems and disadvantages of the prior art and achieves the aforementioned objects in accordance with the purpose of the invention by providing a nonwoven composite material having a basis weight ranging from approximately 1–3 oz/yd$^2$ suitable for use as a sterilization wrap. The composite material comprises a layer of a meltblown fabric of thermoplastic polymeric microfibers having an average fiber diameter of up to 10 microns and a nominal basis weight ranging from 0.3 to 0.6 oz/yd$^2$ and two prebonded reinforcing fabric layers of thermoplastic polymeric filaments selected from spunbonded, wetlaid and carded webs and having nominal basis weights that may be identical or different and range from 0.3 to 2.0 oz/yd$^2$. The meltblown fabric layer and the reinforcing fabric layers are positioned in juxtaposed surface-to-surface relationship, with the meltblown fabric layer positioned between the reinforcing fabric layers. All of these layers are continuously-bonded together in a nip of double helical grooved rolls by the application of heat and pressure to form a composite material having areas of heavy bonding, areas of intermediate bonding and areas of light bonding.

In a preferred embodiment of the present invention, the reinforcing fabric layers of thermoplastic polymeric filaments are spunbonded and both the meltblown fabric of thermoplastic polymeric microfibers and the reinforcing fabric layers of thermoplastic polymeric filaments are composed of polypropylene.

The accompanying drawings, which are incorporated in and constitute a part of this specification, illustrate a preferred embodiment of the invention, and together with the description, serve to explain the principles of the invention.

BRIEF DESCRIPTION OF THE DRAWINGS

FIG. 1 is a fragmentary perspective, illustrating the three layers of the nonwoven composite material of the present invention.

DETAILED DESCRIPTION OF THE PREFERRED EMBODIMENT

Reference will now be made in detail to the presently preferred embodiments of the invention, an example of which is illustrated in the accompanying drawings.

In accordance with the present invention as illustrated in FIG. 1, a nonwoven composite material 10 is provided comprising a meltblown fabric layer 12 of thermoplastic polymeric microfibers and two prebonded reinforcing fabric layers 14 and 16 each made of thermoplastic polymer filaments.

The preferred thermoplastic polymeric microfibers used to form meltblown fabric layer 12 are polypropylene, nylon 6, nylon 6,6, polybutylene terephthalate, polyethylene, polyethylene terephthalate, linear low density polyethylene, and copolymers, composites and blends thereof, the most preferred being polypropylene. Meltblown fabric layer 12 can be prepared by known techniques such as the process described in U.S. Pat. No. 3,978,185 to Buntin et al. which is incorporated herein by reference in its entirety and *Industrial and Engineering Chemistry*, Vol. 48, No. 8 (1965), pp. 1342–1346. Briefly, the process involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven mat.

Reinforcing fabric layers 14 and 16 made of the thermoplastic polymer filaments are preferably spunbonded, wet laid or carded webs, and most preferably are spunbonded webs. Methods for producing spunbonded webs are disclosed in U.S. Pat. Nos. 3,338,992 and 3,341,394 to Kinney; 3,276,944 to Levy; 3,502,538 to Peterson; 3,502,763 and 3,509,009 to Hartmann; 3,542,615 to Dobo et al. and 3,692,618. The method generally involves continuously extruding a thermoplastic polymer through a spinneret to form discrete filaments. The filaments are drawn to achieve molecular orientation and tenacity. The continuous filaments are then deposited in a substantially random manner onto, for example, a carrier belt, to form a web of substantially continuous and randomly arranged, molecularly oriented filaments. Reinforcing fabric layers 14 and 16 of the invention are prebonded and thus have a structural integrity of their own. The preferred thermoplastic polymer filaments used to make reinforcing fabric layers 14 and 16 are polypropylene, nylon 6, nylon 6,6, polybutylene terephthalate, polyethylene, polyethylene terephthalate, linear low density polyethylene, and copolymers, composites and blends thereof, with the most preferred being polypropylene.

In accordance with the invention, meltblown fabric layer 12 juxtaposed surface-to-surface relationship, with meltblown fabric layer 12 positioned between reinforcing fabric layers 14 and 16. All three of these fabric layers are then continuously-bonded together by the application of heat and pressure to form composite material 10.

Figure 2:
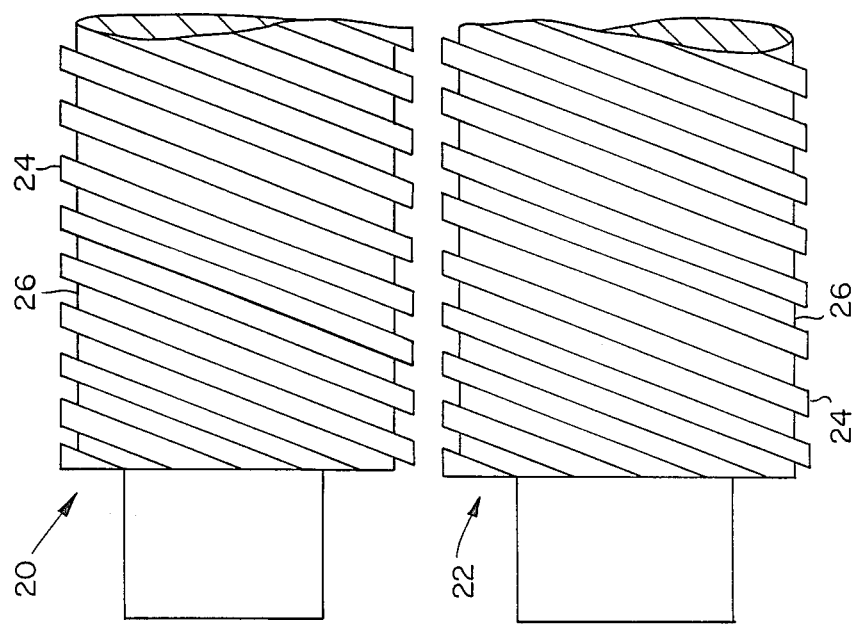
FIG. 2 illustrates a pair of rolls that can be used to make the type of bonding pattern illustrated by FIG. 3.

In accordance with the invention as illustrated in FIG. 2, the nonwoven composite material of the invention is made by embossing the three-layered structure by passing it between a pair of rolls 20 and 22 which are engraved with a pattern of lands 24 and grooves 26 in helical arrangement. The method that is used to produce the nonwoven composite material of the present invention is disclosed by U.S. Pat. No. 3,507,943 which is incorporated herein by reference in its entirety.

Figure 3:
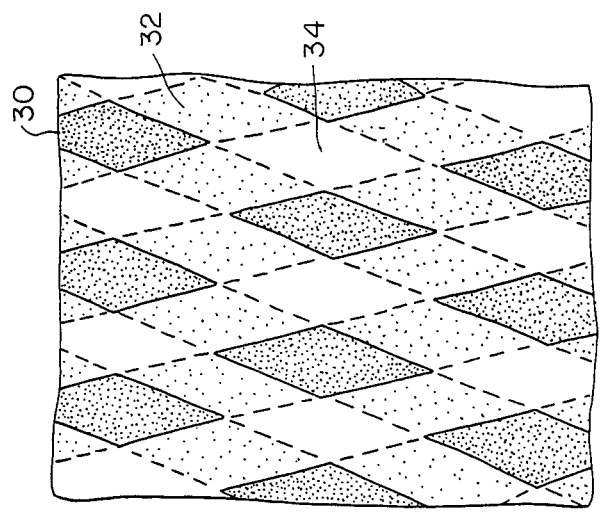
FIG. 3 is an illustration of one type of pattern produced by the continuous bonding process utilized to make the nonwoven composite material of the present invention.

In accordance with the invention as illustrated by FIG. 3, the nonwoven composite material 10 of the invention has areas of heavy bonding 30, areas of intermediate bonding 32, and areas of light bonding 34.

Areas of heavy bonding 30 are produced on those areas of nonwoven composite material 10 that are contacted on one side by land 24 from upper roll 20 and on the other side by land 24 from lower roll 22. Areas of intermediate bonding 32 are produced on nonwoven composite material 10 in those areas that are contacted on one side by groove 26 from one of either upper or lower rolls 20 and 22 and contacted by land 24 from the other of upper or lower rolls 20 and 22. Areas of light bonding 34 are produced in those areas that are contacted on each side by groove 26 from both upper roll 20 and lower roll 22.

The bonding process utilized to make the nonwoven composite material of the present invention results in a material that has a continuous bonding pattern. The nonwoven composite material should contain a minimal number of loose fibers. It is believed that this would be the case in part because of the continuous bonding pattern but predominantly because the spunbonded surface of the composite material is bonded twice, once by the original prebonding step and again at thermal lamination to the meltblown fabric layer. Minimizing the presence of loose fibers is advantageous, particularly when the composite material of the invention is to be utilized as a sterilization wrap for medical items.

Also, since the spunbonded reinforcing layers of the fabric of the present invention are bonded twice, once by the original prebonding step and again at the thermal lamination to the meltblown layer, this would be expected to prevent the presence of long filament strands that would tend to "fuzz-up" during use of the material. Thus, abrasion resistance that is superior to that of either discrete or continuous line bond patterns would be expected.

In addition, unexpectedly good tear resistance is achieved by the nonwoven composite material of the invention. Up to now, nonwoven materials produced by continuous bonding processes have suffered from unfavorable tear resistance as compared to nonwovens produced by discrete bonding processes. Also, it would be expected that nonwoven composite materials composed of prebonded layers would suffer from unfavorable tear resistance as compared to non-prebonded nonwoven composites. (See Example 2). The tear resistance of the composite material of the invention having a continuous bonding pattern and having prebonded reinforcing layers is compared to that of discretely bonded, non-prebonded composites in Example 1. The results surprisingly show that the tear resistance of the material of the present invention is as good as that of comparable discretely bonded materials with non-prebonded reinforcing layers.

Comparable tear resistance is achieved by the nonwoven composite material of the present invention while maintaining a "softness" or "stiffness" as measured by handle and drape that is at least comparable to that of similar prior art nonwovens produced by discrete bonding. (See Example 1).

An additional advantage of the present invention results from the reinforcing fabric layers being prebonded prior to the thermal lamination step that results in the nonwoven composite material. Prebonded reinforcement webs offer processing flexibilities in that the basis weights of the respective reinforcing fabric layers can be manipulated in order to achieve specific properties for both the composite material and for each side thereof. Moreover, the flexibility of the process using prebonded webs allows for the use of different nonwoven technologies for producing the reinforcing fabrics, such as wetlaying or carding as well as spunbonding. Furthermore, various combinations of different polymers can be selected for use in the reinforcing fabric layers to further manipulate end-fabric properties of the nonwoven composite material.

In accordance with a particularly preferred embodiment of the present invention, the nonwoven composite material is utilized as a sterilization wrap for surgical instruments and other health care supplies. Fabrics useful for these purposes must permit penetration of a sterilant, must be capable of impeding the passage of bacteria and other contaminants to a high degree, and also should be fluid repellent. The nonwoven composite material of the present invention satisfies these criteria.

The nonwoven composite material of the invention is useful as a sterilization wrap for sterile gloves, syringes, and surgical instruments and packs. It could also be used for surgical caps, gowns, surgical table and Mayo stand covers, isolation gowns, scrub apparel and industrial garments and fabrics, and the like.

the force required to propagate a tongue-type tear in a material, starting from a cut in the material. Handle-O-Meter measurements were determined in accordance with TAPPI T-498 utilizing a Thwing-Albert Handle-0-Meter, Model 211-5. The Handle-O-Meter measures the force required to push a fabric specimen into a slot having parallel edges by means of a moving blade. Water impact penetration was determined in accordance with AATCC 42-1985, which utilizes a textile blotting paper to measure the amount of water sprayed onto a subject material that penetrates that material.

The results, as presented in Table 1, represent the average values for 30 samples and demonstrate that the composite material of the present invention has comparable tear resistance, as measured by Elmendorf tear strength, compared to that of the Kimguard material and also has comparable "softness" or "stiffness" as measured by handle and drape. This is the case, even though the composite material of the present invention is continuously-bonded and the prior art material is discretely bonded.

TABLE 1

| Properties | JR-1 | JR-2 | JR-3 | JR-4 | Kimguard Heavy Duty | Kimguard Regular Duty |
|---|---|---|---|---|---|---|
| Basis Wt. (oz./yd$^2$) | | | | | | |
| components S | 1.0 | 1.0 | .55 | .43 | | |
| M | .6 | .3 | .6 | .6 | | |
| S | 1.0 | .43 | .55 | .43 | | |
| composite mat'l | 2.76 | 1.80 | 1.75 | 1.52 | 1.93 | 1.26 |
| Elmendorf tear (gr.) | | | | | | |
| MD | 969 | 492 | 379 | 218 | 496 | 263 |
| CD | 1486 | 735 | 453 | 359 | 542 | 253 |
| Handle-O-Meter (gr.) | | | | | | |
| MD | 170 | 69 | 54 | 45 | 76 | 28 |
| CD | 97 | 36 | 36 | 19 | 56 | 17 |

MD = machine direction, CD = cross direction
S = spunbonded layer, M = meltblown layer The following examples further illustrate advantageous features of the present invention. The examples should in no way be considered limiting, but are merely illustrative of the various features of the present invention.

EXAMPLE 1

Four samples of the composite material of the present invention were prepared. The samples were prepared by bonding one sheet of meltblown fabric made from Polyweb ® polypropylene between two sheets of spunbonded fabric made from Celestra ® polypropylene. The three layers were bonded together by the process disclosed in U.S. Pat. No. 3,507,943, utilizing a pair of helically arranged heated rolls as shown in FIG. 2. The rolls were maintained at temperatures ranging between 289°–294° F. The material was fed between the rolls at a speed ranging between 25–55 ft./min. and the pressure exerted by the rolls was 714 lb/lineal in. for JR-1 and JR-2 and 535 lb/lineal in. for JR-3 and JR-4.

Measurements of tear resistance, handle and water impact penetration of the four continuously-bonded nonwoven composite material samples of the present invention were compared with two samples of conventional, discretely bonded material marketed by Kimberly-Clark under the trade name Kimguard ® and believed to be covered by U.S. Pat. No. 4,041,203 to Brock et al.

Basis weights of the materials were determined in accordance with ASTM D-3776-85. Elmendorf tear strength was determined in accordance with ASTM D-1424-83, which utilizes a falling pendulum to measure

EXAMPLE 2

Three samples of composite were prepared in the same manner as the samples in Example 1. One of the samples, 14486-01, was prepared using spunbonded fabric of Celestra ® polypropylene that had not been prebonded. The other two samples, 14486-02 and 14486-03, were prepared using Celestra ® polypropylene fabric that had been prebonded at 6% and 18% bond areas, respectively. The Celestra was 1.0 oz/yd$^2$ and the Polyweb ® polypropylene meltblown fabric used to form the composite material was 0.6 oz/yd$^2$.

| Composite bonding conditions: | temperature: | 286–290° F. |
|---|---|---|
| | pressure: | 625 pli (pounds per lineal inch) |
| | line speed: | 15–20 fpm (feet per minute) |

The trapezoid tearing load of each sample was determined in accordance with ASTM Method D1117, Section 14. The trapezoid tear test is used to determine the tearing resistance of nonwoven fabrics, which property is derived from the bonding and interlocking of the fibers and from the physical properties of the fibers themselves.

The results, as presented in Table 2, demonstrate that the effect of prebonding the spunbonded reinforcing layers of Celestra ® is to decrease the tear strength of the resulting composite fabric. The greater degree of prebonding in sample 14486-03 (18% vs 6% for 14486-02) results in even lower composite tear strength for 14486-03 than for 14486-02.

TABLE 2

|  | 14486-01 unbonded Celestra ® (3.1 oz/yd²) | 14486-02 Celestra ® prebonded at 6% (2.9 oz/yd²) | 14486-03 Celestra ® prebonded at 18% (3.2 oz/yd²) |
| --- | --- | --- | --- |
| Trapezoid tear of composite fabric (lbs) | | | |
| MD | 24.5 | 14.9 | 12.6 |
| CD | 14.5 | 8.0 | 6.8 |

MD = machine direction,
CD = cross direction

It is clear from the data presented in Table 2 that prebonding the spunbonded reinforcing layers has the effect of reducing the tear strength of the composite fabric. This is probably due to the greater degree of fiber immobilization caused by prebonding. Immobilization of the fibers within a nonwoven structure results in tear stresses not being distributed throughout the fabric, and results in lower tear strength.

Similarly, it might be expected that the relatively high degree of fiber immobilization effected by the continuous line bonding process utilized to produce the composite material of the present invention would also be responsible for a corresponding decrease in fabric tear strength. Instead, Example 1 illustrates that the combination of utilizing a continuous bond pattern with prebonded reinforcing layers results in a surprisingly high tear resistance of the resulting composite material, comparable to that of commercial products utilizing non-prebonded reinforcing layers and a discrete bonding pattern. It is postulated that this is due to the fact that the continuous bond pattern acts to inhibit and redirect tear lines rather than stopping them completely. Tear stresses are then effectively distributed throughout the structure, and the dimensional stability realized by prebonding the reinforcing layers allows for the unexpectedly high fabric tear strength of the composite material.

Although the present invention has been described in connection with the preferred embodiments, it is understood that modifications and variations may be resorted to without departing from the spirit and scope of the invention. Such modifications are considered to be within the purview and scope of the invention and the appended claims.

What is claimed is:

1. A nonwoven composite material having a basis weight ranging from 1-3 oz/yd², suitable for use as a sterilization wrap, comprising:

a layer of a meltblown fabric of thermoplastic polymeric microfibers having an average fiber diameter of up to 10 microns and a basis weight ranging from 0.3 to 0.6 oz/yd²;

two prebonded reinforcing fabric layers of thermoplastic polymer filaments selected from spunbonded, wetlaid and carded webs and having basis weights that may be identical or different and range from 0.3 to 2.0 oz/yd²;

wherein said meltblown fabric layer and said reinforcing fabric layers are positioned in juxtaposed surface-to-surface relationship, said meltblown fabric layer positioned between said reinforcing fabric layers, and wherein all of said layers are continuously-bonded together in a nip of double helical grooved rolls by the application of heat and pressure to form a composite material having areas of heavy bonding, areas of intermediate bonding and areas of light bonding.

2. The nonwoven composite material of claim 1, wherein said thermoplastic polymeric microfibers used to form the meltblown fabric are selected from polypropylene, nylon 6, nylon 6,6, polybutylene terephthalate, polyethylene, polyethylene terephthalate, linear low density polyethylene, and copolymers, composites and blends thereof.

3. The nonwoven composite material of claim 2, wherein said thermoplastic polymeric microfibers are polypropylene.

4. The nonwoven composite material of claim 1, wherein said thermoplastic polymer filaments used to form the reinforcing fabric layers are selected from polypropylene, nylon 6, nylon 6,6, polybutylene terephthalate, polyethylene, polyethylene terephthalate, linear low density polyethylene, and copolymers, composites and blends thereof.

5. The nonwoven composite material of claim 4, wherein said thermoplastic polymer filaments are polypropylene.

6. The nonwoven composite material of claim 1, wherein said reinforcing fabric layers of thermoplastic polymer filaments are spunbonded.

7. The nonwoven composite material of claim 6, wherein said thermoplastic polymer filaments used to make the reinforcing fabric layers have an average filament diameter greater than 12 microns.

8. The nonwoven composite material of claim 7, wherein said filaments have an average filament diameter ranging between 12 and 55 microns.

9. The nonwoven composite material of claim 6, wherein the ratio of the meltblown fabric layer to the spunbonded reinforcing fabric layers ranges from 0.075:1 to 1:1 by weight.

10. The nonwoven composite material of claim 9, wherein said ratio of meltblown layer to spunbonded layers ranges from 0.2:1 to 0.7:1.

* * * * *